(12) United States Patent
Altendorf et al.

(10) Patent No.: US 7,723,657 B2
(45) Date of Patent: May 25, 2010

(54) FOCUS DETECTION APPARATUS HAVING EXTENDED DETECTION RANGE

(75) Inventors: Eric Herbert Altendorf, Everett, WA (US); Scott Harsila, Bothell, WA (US); Matthew David Watson, Bellevue, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 0 days.

(21) Appl. No.: 12/345,566

(22) Filed: Dec. 29, 2008

(65) Prior Publication Data

US 2009/0152440 A1 Jun. 18, 2009

Related U.S. Application Data

(63) Continuation-in-part of application No. 11/941,805, filed on Nov. 16, 2007, now abandoned.

(51) Int. Cl.
*G02B 7/04* (2006.01)
(52) U.S. Cl. .................... 250/201.2; 250/559.4
(58) Field of Classification Search ... 250/201.2–201.5, 250/201.9, 559.4, 559.3, 559.22; 359/368, 359/383–389, 379; 356/614, 601, 399–401
See application file for complete search history.

(56) References Cited

U.S. PATENT DOCUMENTS

| | | |
|---|---|---|
| 3,161,718 A | 12/1964 | De Luca |
| 4,336,997 A | 6/1982 | Ross |
| 4,950,878 A | 8/1990 | Ulich |
| 5,055,663 A | 10/1991 | Morimoto |
| 5,113,386 A | 5/1992 | Whitehead |

(Continued)

FOREIGN PATENT DOCUMENTS

DE 4335249 A1 4/1994

(Continued)

OTHER PUBLICATIONS

"QVPAK 3D CNC Vision Measuring Machine: User's Guide," Version 7.1, 2d ed., Manual No. 99MCB225A1, Series No. 359, Mitutoyo Corporation & Micro Encoder Inc., Kanagawa, Japan, Sep. 2003.

(Continued)

*Primary Examiner*—Que T Le
(74) *Attorney, Agent, or Firm*—Christensen O'Connor Johnson Kindness PLLC

(57) ABSTRACT

An extended range focus sensor is provided. In various embodiments, the focus sensor may include a relay lens assembly to image a plane between an objective lens and the relay lens arrangement to a plane near an entrance pupil of a focus detector arrangement of the focus sensor. In some embodiments, the objective lens pupil is imaged onto the focus detector entrance pupil. In some embodiments, an illumination beam passes through the relay lens arrangement and is magnified on its way to be output by the objective lens, and the reflected focus detection beam passes back through the objective lens and the relay lens arrangement and is reduced prior to being input to the focus detector arrangement. In some embodiments, the focus detector arrangement may comprising a broad range focus detector combined with a high resolution Shack-Hartmann focus detector, and in others a single extended range Shack-Hartmann focus detector is used.

24 Claims, 9 Drawing Sheets

U.S. PATENT DOCUMENTS

| | | |
|---|---|---|
| 5,283,681 A | 2/1994 | Hoshino |
| 5,973,852 A | 10/1999 | Task |
| 6,184,974 B1 | 2/2001 | Neal |
| 6,369,954 B1 | 4/2002 | Berge |
| 6,541,747 B1 | 4/2003 | Kikuchi |
| 6,550,917 B1* | 4/2003 | Neal et al. ............ 351/221 |
| 6,618,209 B2 | 9/2003 | Nishioka |
| 6,631,020 B2 | 10/2003 | Paris |
| 6,750,436 B2 | 6/2004 | Feldman |
| 6,856,381 B2 | 2/2005 | Christoph |
| 6,897,421 B2 | 5/2005 | Gelman |
| 6,930,838 B2 | 8/2005 | Schachar |
| 7,016,525 B2 | 3/2006 | Gladnick |
| 7,071,451 B2* | 7/2006 | Ishikawa et al. ...... 250/201.4 |
| 7,348,528 B2* | 3/2008 | Marshall ............ 250/201.3 |
| 7,436,587 B2 | 10/2008 | Feldman |
| 7,455,407 B2 | 11/2008 | Neal |
| 2008/0100850 A1 | 5/2008 | Watson |

FOREIGN PATENT DOCUMENTS

| | | |
|---|---|---|
| JP | 5-164556 | 6/1993 |

OTHER PUBLICATIONS

European Examination Report mailed Nov. 6, 2008, issued in Application No. EP 08005386.1, filed Mar. 20, 2008.

Kerr, T., "Telescope Focus," Joint Astronomy Centre, Nov. 7, 2004, <http://www.jach.hawaii.edu/UKIRT/telescope/focus.html>, 3 pages.

QVPAK 3D CNC Vision Measuring Machine Operation Guide, Version 2.0, Manual No. 4911GB, Series No. 359, Mitutoyo Corporation & Micro Encoder Inc., Kanagawa, Japan, Sep. 1996.

* cited by examiner

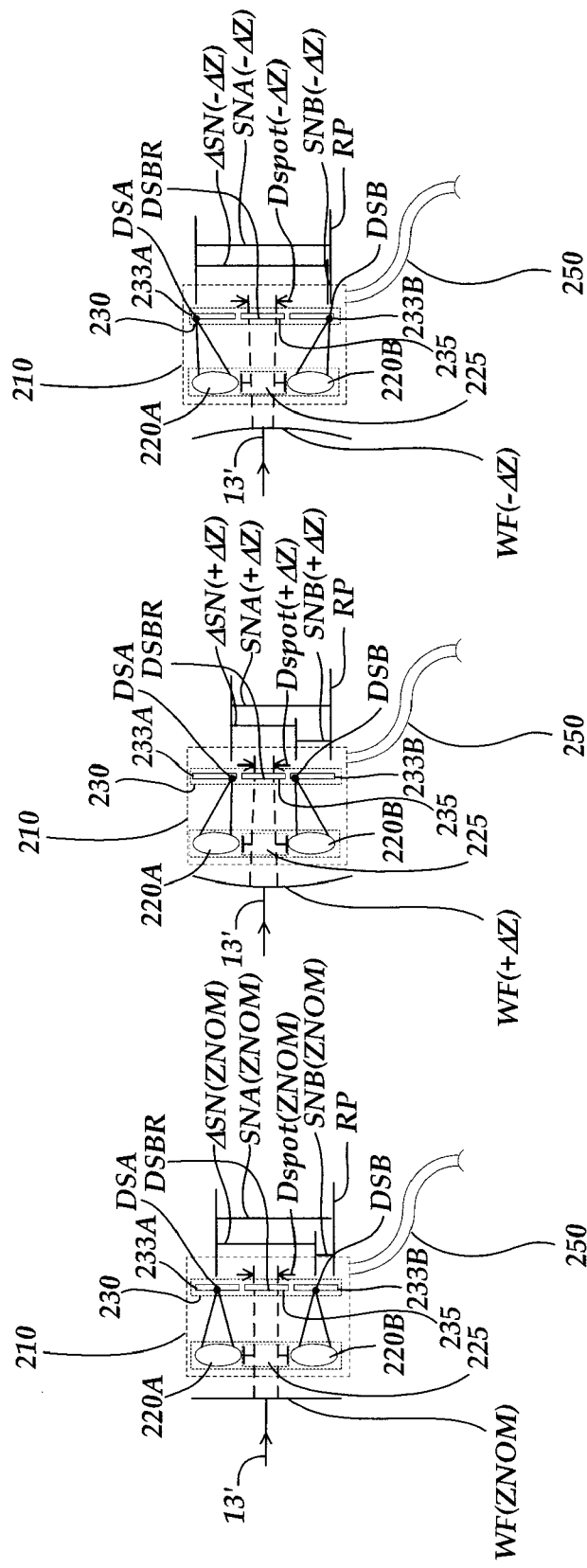
*Fig.2A.* *Fig.2B.* *Fig.2C.*

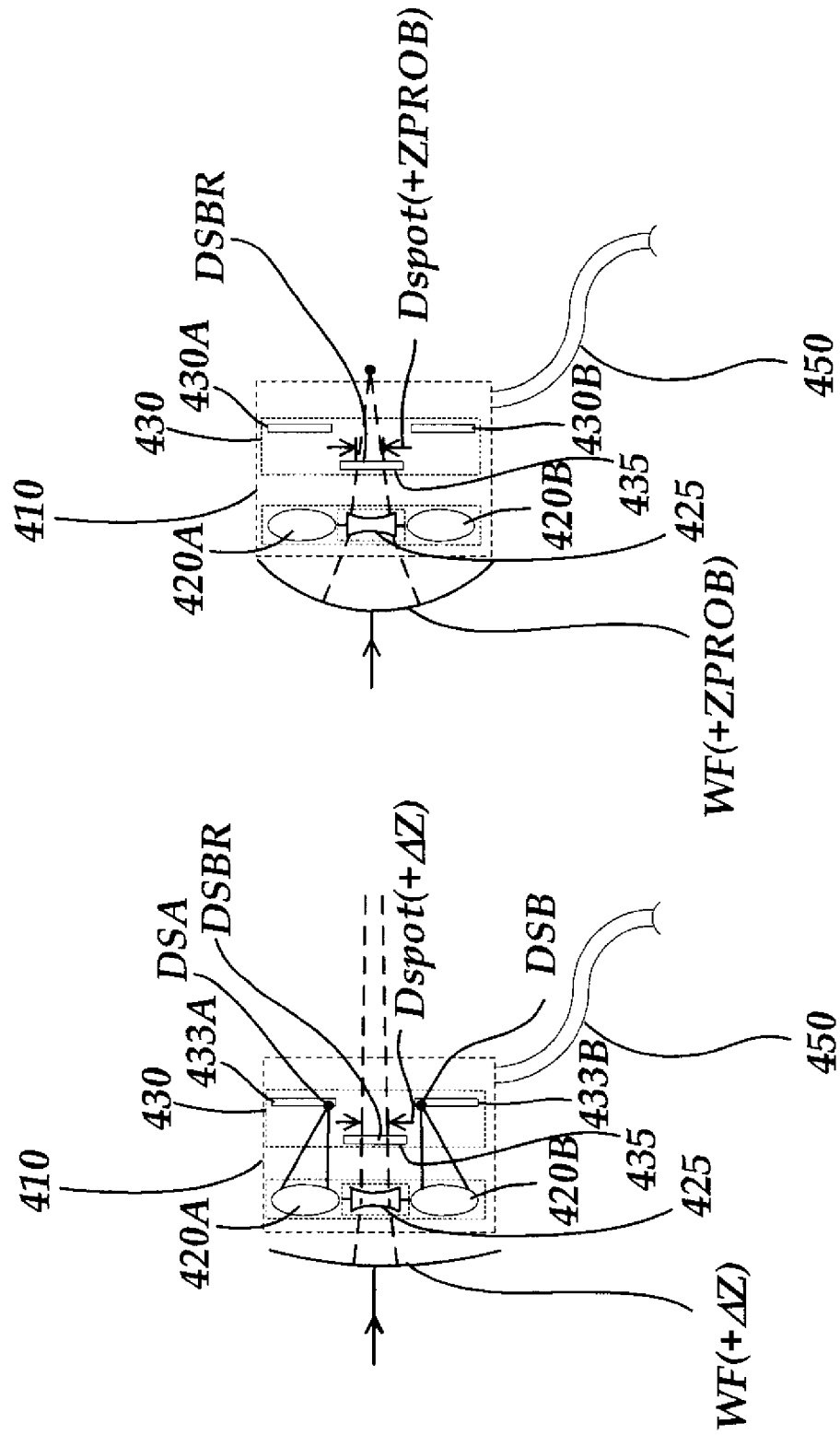

FOCUS DETECTION APPARATUS HAVING EXTENDED DETECTION RANGE

CROSS-REFERENCE TO RELATED APPLICATION

This application is a continuation-in-part of U.S. patent application Ser. No. 11/941,805, filed Nov. 16, 2007, priority from the filing date of which is hereby claimed under 35 U.S.C. §120, the disclosure of this application is hereby incorporated by reference herein.

FIELD OF THE INVENTION

The invention relates generally to machine vision inspection systems, and more particularly to an extended range non-contact surface height and focus sensor that may be utilized as part of a machine vision inspection system.

BACKGROUND OF THE INVENTION

Precision machine vision inspection systems (or "vision systems" for short) can be used to obtain precise dimensional measurements of inspected objects and to inspect various other object characteristics. Such systems may include a computer, a camera and microscope-type optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, which is hereby incorporated by reference in its entirety. Such systems are known to incorporate various types of focus measurement, for governing autofocus and/or surface height measurements. One known type of focus measurement is based on analysis of the contrast in acquired images. For a given field of view, the highest contrast image generally corresponds to the best focused image. A surface height measurement may be inferred from the best focused image position, since the camera-object distance corresponding to any image is generally known in precision machine vision inspection systems.

Another type of focus and/or measurement is based on the use of an auxiliary focus sensor, which is a focus sensor that does not rely on the images of the machine vision inspection system for determining the best focus position or surface height. Various known types of auxiliary focus sensors have been used including triangulation sensors, knife edge focus sensors, chromatic confocal sensors, and the like. However, such known auxiliary sensors have exhibited deficiencies such as inadequate range vs. resolution capability, and/or inadequate robustness when tracking over abrupt steps in surface height.

One type of sensor for measuring changes of distance to a workpiece surface from an objective lens is described in U.S. Pat. No. 4,336,997, to Röss et al., which is hereby incorporated by reference in its entirety. The '997 patent discloses a configuration in which an objective lens may be focused on a measurement object, and a focus detector (e.g., a modal aperture stop located in front of a photoelectric converter, at a detector focus plane) may indicate deviations of the measurement object from the plane of best focus. However, the '997 patent does not disclose a focus detector with an unconventional range vs. resolution capability.

To obtain high resolution measurements of surface shape, a Shack-Hartmann type of wavefront sensing technique has been used. U.S. Pat. No. 6,184,974, to Neal et al., which is hereby incorporated by reference in its entirety, discloses that minute deviations of a surface from perfect flatness, such as the surface of a silicon wafer, etc., may be measured by reflecting appropriate illumination from the surface and directing it to a Shack-Hartmann wavefront sensor that includes a plurality of sub-apertures. However, the plurality of sub-apertures sense a relative surface profile, they do not sense an overall range (distance) to a surface, and the '974 patent does not disclose a detector configuration with an unconventional range vs. resolution capability.

U.S. Pat. No. 4,950,878, to Ulich et al., which is hereby incorporated by reference in its entirety, discloses an adaptive optics wavefront control system including a Shack-Hartmann type of wavefront sensing technique called a coarse/fine gradient sensor, comprising two Schack-Hartmann type sensors having different focal lengths and a different ranges and sensitivities. The configuration of the '878 patent provides an unconventional range vs. resolution capability. However, while the configuration of the '878 patent is suited for adaptive optics control, it is not well suited to the physical design constraints and the range requirements of a precision machine vision inspection system of the type outlined above.

A focus and/or range sensor that overcomes the foregoing and other disadvantages, would be desirable.

SUMMARY OF THE INVENTION

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention is directed to a focus and range detection apparatus and method with an extended range vs. resolution capability, and having a configuration that is of particular utility in a general purpose microscopic machine vision inspection system for performing precision dimensional metrology. The focus and range detection apparatus may also be referred to simply as a focus sensor. The focus sensor provides focus detection and/or range signals that depend on the location of a workpiece surface within a sensing range along a direction approximately parallel to the optical axis of an objective lens.

According to one embodiment of the invention, the focus sensor comprises a novel dual range focus detector arrangement. The focus sensor further comprises an illumination source, a collimation lens, an objective lens, and a beam splitting surface. In operation, the collimation lens is arranged to input radiation from the illumination source and output an illumination beam having a fixed degree of collimation or near collimation. The objective lens is arranged to input the illumination beam and to focus the illumination beam at a nominal focus plane along an optical axis of the focus sensor and to receive and transmit a reflected beam reflected from a workpiece surface located along the optical axis. The beam splitting surface is positioned along the illumination beam between the objective lens and the collimation lens, and along the reflected beam between the objective lens and the dual range focus sensor. The dual range focus detector arrangement is positioned along the optical axis to receive light from the reflected beam that is transmitted by the objective lens and the beamsplitting surface.

As used herein, the term optical axis generally refers to the central line of an optical path of a focus sensor and its dual range focus detector arrangement, as outlined further below. It is not used in a narrow sense (e.g., simply as the axis of a lens element or the like) unless indicated by context. The central line of the optical path may generally coincide with the optical axis of an objective lens and a central axis of the dual range focus detector arrangement. The optical path may be bent or deflected, and similarly for its optical axis.

According to another embodiment of the invention, the novel dual range focus detector arrangement comprises a broad range focus detector configuration configured according to a first focus detection principle, and a high resolution focus detector configuration configured according to a second focus detection principle that is different from the first focus detection principle. The broad range focus detector may include a broad range focus detector sub-aperture located proximate to the optical axis, and a photodetector that receives light from that sub-aperture. In various embodiments, the optical axis passes through the broad range focus detector sub-aperture. The broad range focus detector is configured to provide a broad range focus and/or range signal that varies monotonically over a first focus detection range of the focus sensor. The high resolution focus detector comprises a Shack-Hartmann configuration that includes at least one sub-aperture lens located proximate to the broad range focus detector sub-aperture and located away from the optical axis, and a photodetector that receives light from that lens. The high resolution focus detector is configured to provide a high resolution focus and/or range signal over a second focus detection range that is smaller than, and located within, the first focus detection range.

According to another embodiment of the invention, the high resolution focus detector comprises at least first and second sub-aperture lenses and corresponding photodetectors, all arranged to provide at least two wavefront detectors that provide respective signals, wherein a relationship between the at least two respective signals is indicative of a wavefront curvature of the reflected beam at the high resolution focus detector.

According to another embodiment of the invention, the broad range focus detector comprises a focus-altering lens that that receives the light that is transmitted through the broad range focus detector sub-aperture and transmits that light to the photodetector element. In various embodiments, the focus-altering lens is configured to focus the reflected beam at a focus point beyond a detection plane of the photodetector element, for all reflected beams corresponding to the first focus detection range. In other embodiments, the focus-altering lens is configured to focus the reflected beam at a focus point between the detection plane of the photodetector element and the focus-altering lens, for all reflected beams corresponding to the first focus detection range. In one embodiment, the focus-altering lens may coincide with and/or provide the broad range focus detector sub-aperture.

The dual range focus detection arrangements outlined herein include previously unknown and particularly advantageous combinations of features. For example, the region of the wavefront proximate to the optical axis is advantageously used for a broad range focus detector configuration that is of a different type than a Shack-Hartmann configuration, even the though Shack-Hartmann configuration may be used for the high resolution portion. This is advantageous because a Shack-Hartmann sub-aperture along the optical axis would be relatively insensitive to wavefront curvature, and various broad range focus detector configurations may have a simpler configuration or more reliable operation by having their input sub-aperture along the optical axis. Conversely, Shack-Hartmann sub-apertures located away from the optical axis are sensitive to wavefront curvature, as desired for the high resolution focus detection configuration. Furthermore, in the disclosed combination of these features, the sub-apertures of the broad range and high resolution focus detection configurations may all sample the same wavefront without requiring beamsplitting surfaces or the like. In addition, a single detector array may provide all measurement signals associated with each of the sub-apertures, in some embodiments according to this invention.

In various embodiments of the invention, the focus sensor comprises a relay lens arrangement located along the optical axis between the objective lens and the focus detector arrangement to input the reflected beam that is transmitted by the objective lens and to output the reflected beam to be input by the focus detector arrangement. In some embodiments, the relay lens arrangement may be located between the beamsplitting surface and the dual range focus detection arrangement. In other embodiments the relay lens arrangement may be located between the beamsplitting surface and the objective lens such that the illumination beam passes through it, as well as the reflected beam. In various embodiments the relay lens arrangement may be configured to magnify the illumination beam and reduce the reflected beam. In various embodiments that use a relay lens arrangement, the focus detector arrangement may be a dual range focus detector arrangement or a single range Shack-Hartmann focus detector arrangement. In either case, the relay lens arrangement may extend the focus detection range of the focus sensor.

In various embodiments, the relay lens arrangement is configured to image a first plane located along the optical axis between the relay lens arrangement and the objective lens to an image plane located in the vicinity of a focus detector entrance pupil of the focus detector arrangement. In some embodiments, the relay lens arrangement may image a plane proximate to an objective lens pupil of the focus sensor, which is located along the optical axis proximate to the objective lens, to a location proximate to a focus detector entrance pupil along the optical axis.

In some embodiments the focus sensor is integrated into a precision machine vision inspection system and the objective lens comprises an objective lens of the precision machine vision inspection system.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 2A, 2B and 2C are diagrams of three cases of wavefront curvature sensed by a first embodiment of a dual range focus detection arrangement;

FIGS. 4A and 4B illustrate a second embodiment of a dual range focus detection arrangement that addresses the potential problem shown in FIGS. 3A and 3B;

DETAILED DESCRIPTION OF THE PREFERRED EMBODIMENT

Figure 1:
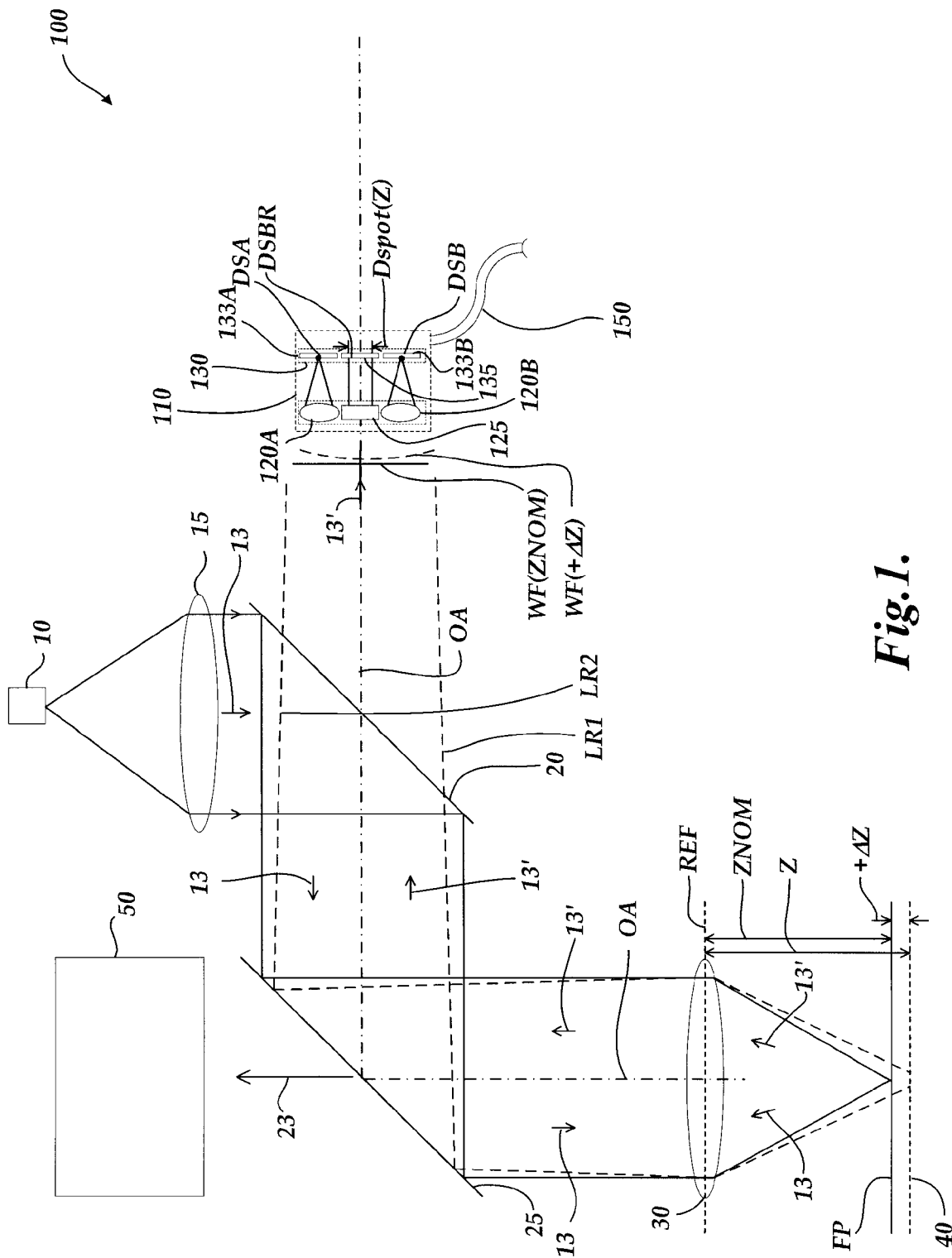
FIG. 1 is a diagram of a first embodiment of a focus sensor in accordance with the present invention which uses a dual range focus detection arrangement.

FIG. 1 is a diagram of first embodiment of a focus sensor 100, which shows a generic embodiment of a dual range focus detection arrangement 110. The focus sensor 100 includes an illumination source 10, a collimation lens 15, a first beamsplitting surface 20, an objective lens 30, and the dual range focus detection arrangement 110. Also shown in FIG. 1 are a second beamsplitting surface 25, a camera 50, a nominal focus plane FP, and a workpiece surface 40. The second beamsplitting surface 25 and the camera 50 are not required elements of the focus sensor 100. Rather, in the arrangement shown in FIG. 1, the focus sensor 100 is integrated with a machine vision inspection system that includes the camera 50, and the second beamsplitting surface 25 facilitates that integration. In particular, the objective lens 30 may be provided by the machine vision inspection system, and may provide workpiece inspection images via the image light 23 transmitted through the second beamsplitting surface 25 to the camera 50. The objective lens 30 may also function as an element of the focus sensor 100, transmitting a reflected beam 13' to be reflected from the second beamsplitting surface 25 along the optical axis OA of the focus detector 100, toward the dual range focus detection arrangement 110, as described in greater detail below. In some embodiments, the image light 23 may be invisible to the focus sensor 100, and the light from the illumination source 10 may be invisible to the camera 50. In other embodiments, the image light 23 and the light from the illumination source 10 may be provided at different times that are synchronized with the operation of camera 50, and the focus sensor 100, respectively. It will be appreciated based on the following disclosure that the focus sensor 100 may also be operated independently, in which case the arrangement may be modified to omit the second beamsplitting surface 25 and the camera 50.

Regarding operation of the focus sensor 100, radiation from the illumination source 10 is input to collimation lens 15 which outputs an illumination beam 13 having a fixed degree of collimation, or near collimation. The illumination beam 13 is then input to the first beamsplitting surface 20, which outputs (and deflects) it to be input to the second beamsplitting surface 25 which outputs (and deflects) it to the objective lens 30. The objective lens 30 inputs the illumination beam 13 and focuses it at a nominal focus plane FP along an optical axis OA. The nominal focus plane FP is located at a distance ZNOM from a reference plane REF that is fixed relative to the objective lens 30.

A workpiece surface 40 may be located along the optical axis OA at a sensed distance Z=ZNOM+ΔZ, as shown in FIG. 1. The workpiece surface 40 reflects the focused illumination beam 13 to provide a reflected beam 13'. The objective lens 30 inputs and transmits the reflected beam 13'. The transmitted reflected beam 13' is then input to the second beamsplitting surface 25, which outputs it (deflects it) to be input by the first beamsplitting surface 20, which outputs it along the optical axis OA where it is input to the dual range focus detection arrangement 110.

Two wavefronts WF(ZNOM) and WF(+ΔZ), which are potential inputs to the dual range focus detection arrangement 110, are illustrated in FIG. 1. The curved wavefront WF(+ΔZ) corresponds to a reflected beam 13' corresponding to the limiting rays LR1 and LR2, arising from a workpiece surface located at a distance+ΔZ from the nominal focus plane FP (e.g., corresponding to the workpiece surface 40, illustrated in FIG. 1). The limiting rays LR1 and LR2 are discussed further below with reference to FIG. 5. The flat wavefront WF(ZNOM) corresponds to a case where a reflected beam 13' arises from a workpiece surface (not shown) located at the nominal focus plane FP. In various embodiments, the dual range focus detection arrangement 110 produces focus and/or range signals that depend on the nominal wavefront curvature of the reflected beam 13', as described in greater detail below.

In various embodiments, the dual range focus detection arrangement 110 includes two portions: a broad range focus detection configuration that operates over a first, broad, focus detection range, and a high resolution focus detection configuration that operates over a second, smaller, focus detection range within the first focus detection range. In general, the broad range focus detection configuration provides a viable low-resolution signal even for a high curvature wavefront corresponding to severely defocused workpiece surfaces at the limits of its broad detection range. The high resolution focus detection configuration will return a viable high-resolution signal(s) for relatively low curvature wavefronts corresponding to workpiece surfaces located proximate to the focus plane FP. As shown in FIG. 1, the broad range focus detection configuration may comprise a sub-aperture element 125 and a photodetector 135 that receives light from the sub-aperture element 125. The received light may form a spot DSBR having a dimension Dspot(Z) on the photodetector 135, as explained in greater detail below. In various embodiments, the broad range focus detector sub-aperture element 125 is arranged such that the optical axis OA passes through it. The broad range focus detector is configured to provide a broad range focus and/or range signal that varies monotonically over its focus detection range. The high resolution focus detection configuration comprises a Shack-Hartmann configuration which, in the embodiment shown in FIG. 1, includes sub-aperture lenses 120A and 120B, located away from the optical axis OA, and photodetectors 133A and 133B that receive light from the lenses 120A and 120B at the spots DSA and DSB, respectively. Optionally, in some embodiments, each of the photodetectors 135, 133A and 133B may be provided by portions of a photodetector array 130, as described in greater detail with reference to FIG. 6. In any case, the photodetectors 135, 133A and 133B may receive power, and output signals to a signal processing and control circuit, (not shown) over a power and signal connection 150.

FIGS. 2A, 2B and 2C are diagrams of three cases of wavefront curvature sensed by a first exemplary embodiment of a dual range focus detection arrangement 210, usable in place of the generic dual range focus detection arrangement 110 of FIG. 1. The components and operation of the detection arrangement 210 are analogous to those of the detection arrangement 110 of FIG. 1 and, in various embodiments, components numbered 2XX in FIG. 2 may be similar or identical to similarly numbered 1XX components in FIG. 1

(e.g., the components 220A and 120A may be similar or identical), except as otherwise described below.

In each of FIGS. 2A-2C, the identical dual range focus detection arrangement 210 comprises a broad range focus detection configuration comprising a sub-aperture element 225 and a photodetector 235, a high resolution focus detection configuration comprising sub-aperture lenses 220A and 220B and photodetectors 233A and 233B, and a power and signal connection 250. In one embodiment, high resolution photodetectors 233A and 233B may comprise lateral effect photodiodes arranged to detect the positions of the spots DSA and DSB. Optionally, in some embodiments, each of the photodetectors 235, 233A and 233B may be provided by portions of a photodetector array 230, as described in greater detail with reference to FIG. 6. In one embodiment, the photodetector 230 may comprise a photodetector array, such as a camera chip, or the like.

Regarding the operation of the broad range focus detector configuration, a portion of the wavefront of reflected beam 13' passes through sub-aperture element 225 will form the spot DSBR on the broad range photodetector 235, which will have a dimension Dspot(Z) that depends on the wavefront curvature and the resulting degree of convergence or divergence of the light that passes through the sub-aperture element 225. The wavefront curvature depends on the variable distance Z (shown in FIG. 1), thus the dimension Dspot(Z) is a function of, and indicates, the variable distance Z. In the embodiment shown in FIGS. 2A-2C, the broad range sub-aperture element 225 comprises a simple aperture (e.g., provided by an aperture mask similar to that described below with reference to FIG. 6). The dimension Dspot(Z) is determined based a signal or signals from the broad range photodetector 235.

Regarding the operation of the high resolution focus detector configuration, another portion of the wavefront of reflected beam 13' is focused by sub-aperture lenses 220A and 220B to form detection spots DSA and DSB at high resolution photodetectors 233A and 233B respectively. According to known Shack-Hartmann techniques, the positions of the detection spots DSA and DSB vary with input wavefront curvature. Signals are provided by the high resolution photodetectors and 233B from which the position coordinates SNA(Z) and SNB(Z) of the detection spots DSA and DSB are determined, according to known techniques. In one exemplary embodiment, the high resolution photodetectors 233A and 233B comprise pixel arrays, the detection spots DSA and DSB may each cover several pixels, and a centroid calculation may provide sub-pixel position interpolation to determine the position coordinate of each detection spot DSA and DSB. In the embodiment shown in FIG. 2, the position coordinates SNA(Z) and SNB(Z) are measured relative to a reference position RP, which the may be arbitrarily selected. In one embodiment, the reference position RP may be designated in accordance with the edge of the photodetector 233B, as shown. A difference measurement $\Delta SN(Z)=SN2(Z)-SN1(Z)$ between the two position coordinates SN2(Z) and SN1(Z), is indicative of the degree of wavefront curvature of reflected beam 13', and may provide a much higher measurement resolution for the wavefront curvature, and the underlying variable distance Z, than the broad range focus detector configuration.

FIG. 2A illustrates a case where the dual range focus detection arrangement 210 inputs a flat wavefront WF(ZNOM), corresponding to a workpiece surface located at Z=ZNOM (that is, at the focus plane FP). In the high resolution focus detector configuration, as a result of the flat wavefront WF(ZNOM), the detection spots DSA and DSB appear on photodetectors 230A and 230B, respectively, at nominal position coordinates SNA(ZNOM) and SNB(ZNOM), aligned with the optical axes of the corresponding sub-aperture lenses 220A and 220B. The resulting difference measurement $\Delta SN$ (ZNOM) indicates that the variable measurement distance Z (shown in FIG. 1) is, in this case, ZNOM. In the broad range focus detector configuration, as a result of the flat wavefront WF(ZNOM), the spot DSBR on photodetector 235 is formed by light that is nominally collimated, and has a nominal spot dimension Dspot(ZNOM), indicating that the wavefront WF(ZNOM) is flat and that the distance Z is ZNOM. The previous description conforms to a convention used herein, wherein the nominal position coordinates are SNA(ZNOM) and SNB(ZNOM), and the nominal spot dimension is Dspot (ZNOM) when the illumination focus height matches the workpiece surface height and the resulting wavefront WF(ZNOM) is flat. Under In general, the wavefront is not flat when the workpiece surface deviates from the focus plane FP.

FIG. 2B illustrates a case where the curvature of a wavefront WF(+$\Delta Z$) is positive, (e.g., similar to the wavefront WF(+$\Delta Z$), corresponding to light rays shown in dashed outline in FIG. 1, which are reflected from the workpiece surface 40 at the distance Z=ZNOM+$\Delta Z$). In the high resolution focus detector configuration, as a result of the curved wavefront WF(+$\Delta Z$), as is known for Shack-Hartmann sensors, the detection spots DSA and DSB appear at positions other than their nominal positions, in this case at the position coordinates SNA(+$\Delta Z$) and SNB(+$\Delta Z$) on photodetectors 230A and 230B, respectively, such that the corresponding difference measurement is $\Delta SN(+\Delta Z)$. $\Delta SN(+\Delta Z)$ is larger than $\Delta SN$ (ZNOM), and indicates that the workpiece surface generating the wavefront is at the distance+$\Delta Z$ beyond the nominal illumination focus distance FD. In the broad range focus detector configuration, as a result of the curved wavefront WF(+$\Delta Z$), the spot DSBR on photodetector 235 is formed by light that is nominally converging, and has a spot dimension Dspot(+$\Delta Z$) that is smaller than Dspot(ZNOM), indicating that the workpiece surface generating the wavefront is at the distance +$\Delta Z$ beyond the nominal illumination focus distance FD.

FIG. 2C illustrates a case where the curvature of a wavefront WF(-$\Delta Z$) is negative. In the high resolution focus detector configuration, as a result of the curved wavefront WF(-$\Delta Z$), as is known for Shack-Hartmann sensors, the detection spots DSA and DSB appear at positions other than their nominal positions, in this case at the position coordinates SNA(-$\Delta Z$) and SNB(-$\Delta Z$) on photodetectors 230A and 230B, respectively, such that the corresponding difference measurement is $\Delta SN(-\Delta Z)$. $\Delta SN(-\Delta Z)$ is smaller than $\Delta SN$ (ZNOM), and indicates that the workpiece surface generating the wavefront is at a distance -$\Delta Z$ closer to the objective lens 30 (shown in FIG. 1) than the nominal illumination focus distance FD. In the broad range focus detector configuration, as a result of the curved wavefront WF(-$\Delta Z$), the spot DSBR on photodetector 235 is formed by light that is nominally diverging, and has a spot dimension Dspot(-$\Delta Z$) that is larger than Dspot(ZNOM), indicating that the workpiece surface generating the wavefront is at the distance -$\Delta Z$ nearer to the objective lens 30 than the nominal illumination focus distance FD.

In each of the FIGS. 2A-2C, the wavefront curvature is small enough that the spots DSA and DSB remain with the range of the high resolution detectors 233A and 233B, respectively, and the high resolution focus detector configuration remains operational. In such cases, the broad range focus detector configuration produces a lower resolution distance measurement that is redundant, and/or superfluous. However, it will be appreciated that for larger wavefront curvatures, when the spots DSA and DSB move off of their respective detectors, the high resolution focus detector configuration becomes inoperative and the lower resolution signals from broad range focus detector configuration may provide essential focus and/or range information to guide focus control operations, or the like. As shown in FIGS. 2B and 2C, the spot dimension Dspot has margin for further dimensional change on the broad range detector 235, so as to produce a useful measurement signal variation even when the spots DSA and DSB are at, or beyond, their respective detector limits. However, for the broad range focus detector configuration shown in FIGS. 2A-2C, the additional measurement range it provides may be relatively limited, for reasons described with reference to FIGS. 3A and 3B.

Figures 3A, 3B:
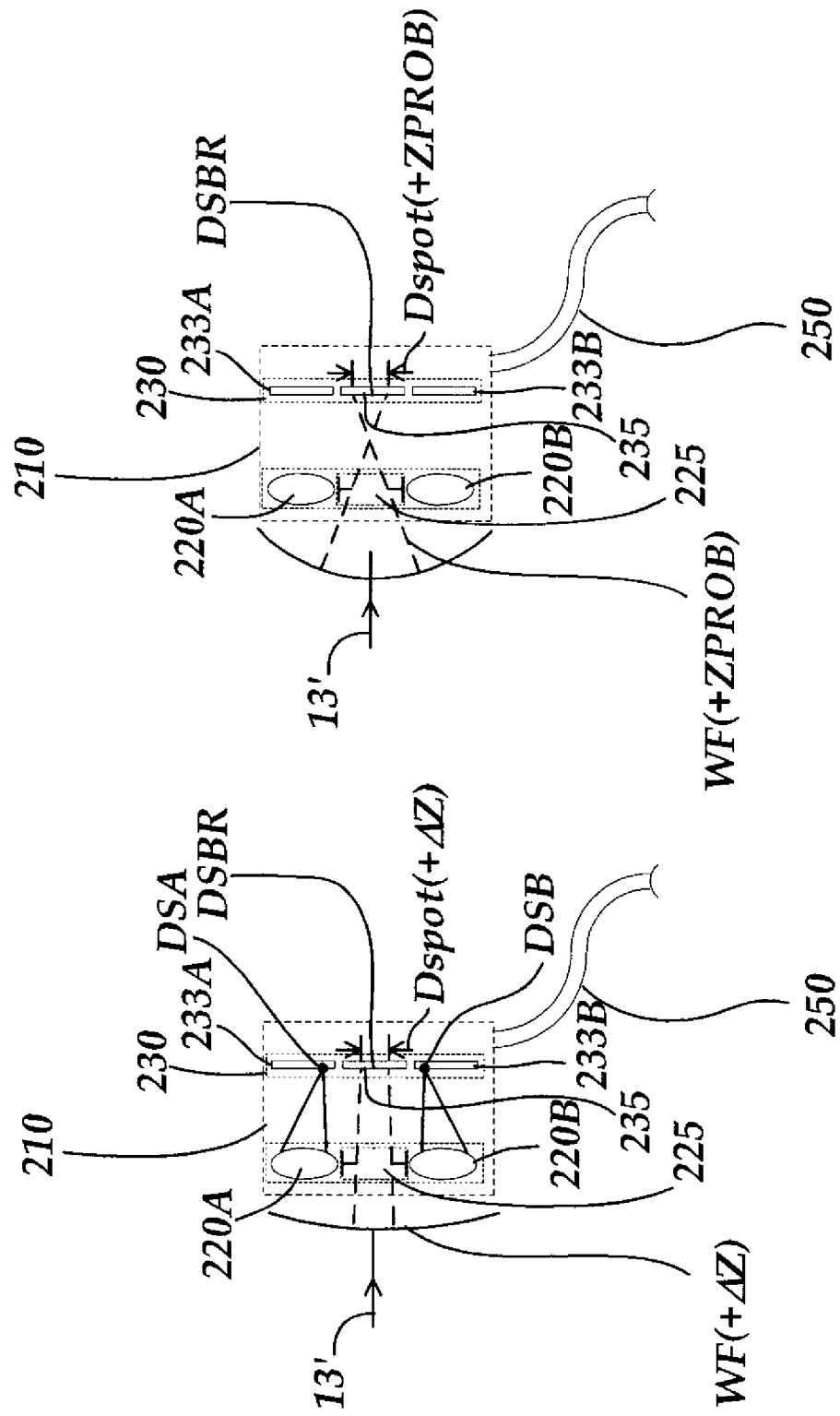
FIGS. 3A and 3B illustrate a potential problem to be avoided in a dual range focus detection arrangement.

FIGS. 3A and 3B illustrate a potential problem to be avoided in a dual range focus detection arrangement, and in particular with the broad range focus detector configuration. FIG. 3A shows the dual range focus detector arrangement 210 with the wavefront WF(+ΔZ) as previously described with reference to FIG. 2B. FIG. 3B shows the dual range focus detector arrangement 210 with a wavefront WF(+ZPROB) having a significantly larger amount of curvature. The curvature of the wavefront WF(+ZPROB) renders the high-resolution focus detector arrangement inoperative, and it would be desirable for the broad range focus detector configuration to provide a useful signal (e.g., a meaningful spot dimension Dspot(+ZPROB)). However, as shown in FIGS. 3A and 3B, two different degrees of wavefront curvature (corresponding to two difference Z-distances, +ΔZ+ZPROB) may give the same spot dimension on the photodetector 235, depending upon the degree of convergence of the rays that pass through the broad range sub-aperture element 225. In particular, if the rays that pass through the sub-aperture element 225 converge strongly enough that they cross, or focus, and then diverge prior to reaching the broad range photodetector 235, to produce a spot dimension similar to that produced by rays that do not cross, then an ambiguous spot dimension, and corresponding ambiguous Z-distance measurement signals, may be created. Stated another way, between (and including) such ambiguous spot dimensions and Z-distance measurement signals, the spot dimensions and Z-distance measurement signals will not change monotonically. To avoid measurement ambiguity, the focus detection range of the dual range focus detection arrangement 210 must be restricted to exclude nonmonotonic measuring signals, limiting its allowable focus detection range. However, the largest practical focus detection range is desirable.

FIGS. 4A and 4B are diagrams of two cases of wavefront curvature sensed by a second exemplary embodiment of a dual range focus detection arrangement 410, usable in place of the dual range focus detection arrangements 110 of FIG. 1, or 210 of FIG. 2. The components and operation of the detection arrangement 410 are analogous to those of the detection arrangement 210, and in various embodiments, components numbered 4XX in FIG. 4 may be similar or identical to similarly numbered 2XX components in FIG. 2 (e.g., the components 420A and 220A may be similar or identical), except as otherwise described below. The components, configuration and operation of the high resolution focus detector configuration (e.g., the components 420A, 420B, 430A and 430B) may be identical, and is not described further.

The dual range focus detection arrangement 410 the addresses the potential range-limiting problem shown in FIGS. 3A and 3B. In particular, in each of the FIGS. 4A and 4B, in the broad range focus detector configuration the broad range sub-aperture element 425 comprises a focus-altering lens. In addition, the broad range photodetector 435 is relatively closer to the sub-aperture 425, in comparison to its counterpart in the dual range focus detection arrangement 210. As a result, as shown in FIG. 4A, the focus altering lens of the sub-aperture element 425 decreases the degree of convergence of the rays of the curved wavefront WF(+ΔZ), and focuses the rays to a position well beyond the detection plane of the photodetector element 435. Similarly, in the as shown in FIG. 4B, the focus altering lens of the sub-aperture element 425 decreases the degree of convergence of the rays of the curved wavefront WF(+ZPROB), and these rays are also focused to a position beyond the detection plane of the photodetector element 435. Thus, in contrast to the ambiguous results described above with reference to FIGS. 3A and 3B, for the same wavefronts WF(+ΔZ) and WF(+ZPROB), the spot dimensions and measurement results from the dual range focus detection arrangement 410, are not ambiguous. For wavefront curvatures between those shown in FIGS. 4A and 4B, the Z-distance measurement signals will change monotonically. Thus, the dual range focus detection arrangement 410, including the focus-altering lens of the sub-aperture element 425, provides a larger broad focus detection range in comparison to the dual range focus detection arrangement 210.

Figure 5:
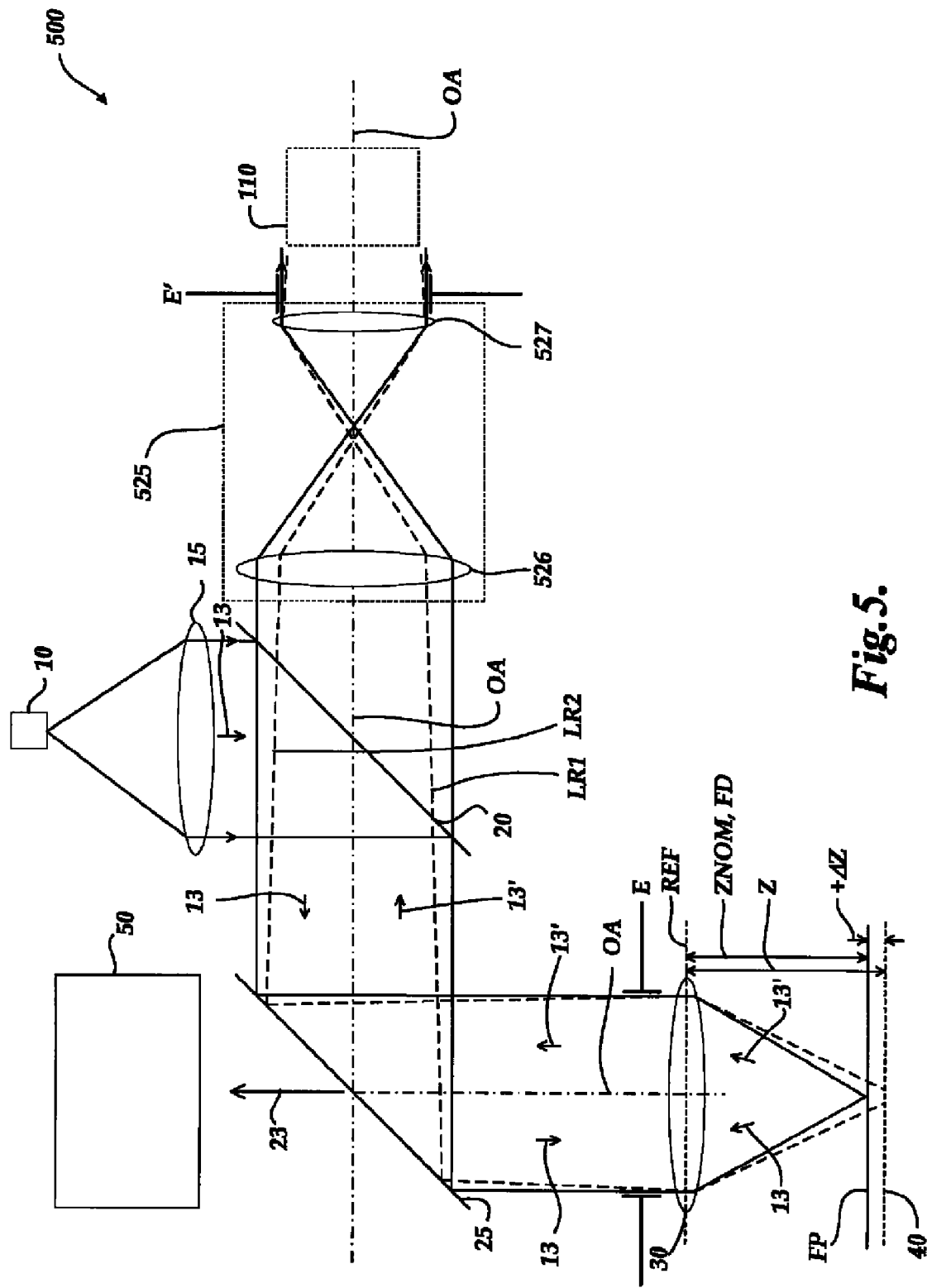
FIG. 5 is a diagram of a second embodiment of a focus sensor in accordance with the present invention which uses a first embodiment of a relay lens arrangement in combination with a dual range focus detection arrangement.

FIG. 5 is a diagram of a second embodiment of a focus sensor 500 in accordance with the present invention, which uses a first embodiment of a relay lens arrangement 525 in combination with a dual range focus detection arrangement 110. The components and operation of the focus sensor 500 are in many respects analogous to those of the focus sensor 100 of FIG. 1 and, in various embodiments; the components in FIG. 5 may be similar or identical to similarly numbered components in FIG. 1. Only the significant differences are described here.

The focus sensor 500 addresses another potential range-limiting problem, and thus extends the range. In particular, as shown in FIGS. 1 and 5, in the case that a workpiece surface is located beyond the focus distance FD (e.g., the surface 40 located as the distance+ΔZ beyond the focus plane FP), the reflected limiting rays LR1 and LR2 will converge. Corresponding to some distance beyond the focus plane FP, for the focus sensor 100 shown in FIG. 1, the convergence will be such that the wavefront available at the input of the dual range focus detector 110 will be so small that it does not fill its sub-apertures, rendering the dual range focus detector arrangement 110 to produce erroneous results, or to be inoperative.

The focus sensor 500 addresses this potential range-limiting problem by including a relay lens arrangement 525, which in this embodiment is positioned proximate to the input of the dual range focus detector arrangement 110. In various embodiments, the relay lens arrangement 525 may include an arrangement of one of more lenses configured such that it images an objective lens pupil E, which is located along the optical axis proximate to the objective lens 30, to the location of a dual range focus detector entrance pupil E', which is located along the optical axis proximate to the input of the dual range focus detector arrangement 110. In the particular embodiment shown in FIG. 5, the relay lens arrangement 525 comprises a first relay lens 526 that is positioned to input the reflected beam 13' from the first beamsplitting surface 20, and transmits it to a second relay lens 527 positioned proximate to at least the broad range detector sub-aperture element of the dual range focus detector arrangement 110. The second relay lens 527 then outputs a wavefront of the reflected beam 13' that approximately fills the dual range focus detector entrance pupil E', regardless of the distance to the workpiece surface, approximately as illustrated in FIG. 5. Thus, the focus sensor 500, including a relay lens arrangement 525, increases at least the broad focus detection range, in comparison to the focus sensor 100, and may also increase the high-resolution focus detection range, in some embodiments. It will be understood the embodiment of the relay lens arrangement 525 shown in FIG. 5 is exemplary only, and not limiting.

Figure 6:
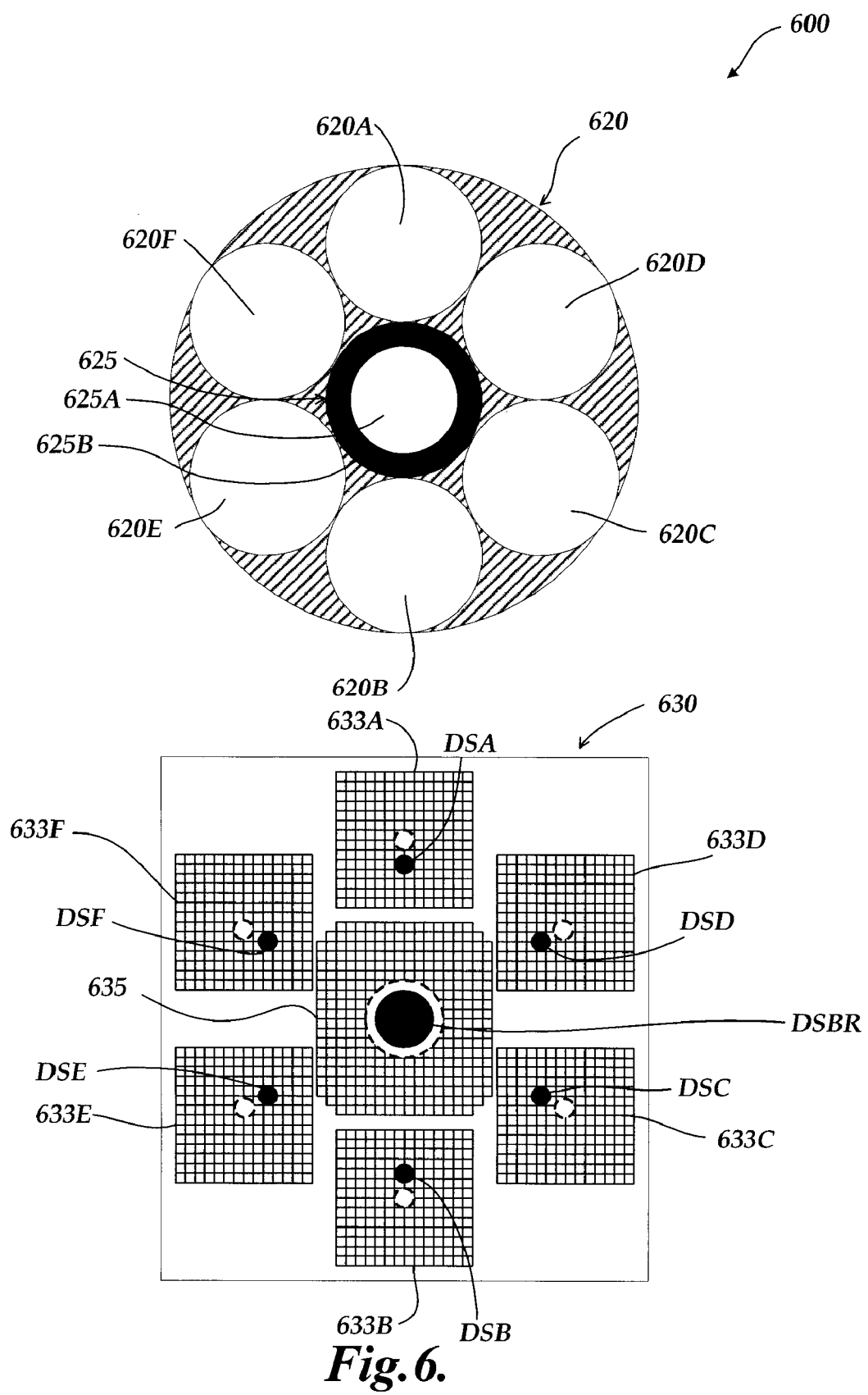
FIG. 6 is a diagram showing various features related to a photodetector element used in various embodiments of a dual range focus detection arrangement.

FIG. 6 is a diagram 600 showing various features related to one exemplary implementation of sub-apertures and photo-detectors usable in a dual range focus detection arrangement. In particular, the diagram 600 shows an exemplary sub-aperture arrangement 620, and corresponding exemplary photodetector arrangement 630. By analogy with previously described embodiments, it will be understood that the center of the sub-aperture arrangement 620 and the center of the photodetector arrangement 630 are aligned along the optical axis in a dual range focus detection arrangement.

The sub-aperture arrangement 620 includes a broad range focus detection configuration sub-aperture element 625 including a light transmitting sub-aperture portion 625A, which may comprise a hole, or a focus-altering lens, in various embodiments. The size of the light transmitting sub-aperture portion 625A may be determined by a surrounding mask element 625B, in some embodiments. The sub-aperture arrangement 620 also includes a plurality of high resolution focus detector configuration sub-aperture lenses 620A-620F. The operation of the sub-aperture lenses 620A-620F illustrated in diagram 600 may be understood based on embodiments outlined in the previous figures, according to known Shack-Hartmann detector principles of operation.

The photodetector arrangement 630 comprises a broad range focus detector configuration photodetector 635, and a plurality of high resolution focus detector configuration photodetectors 633A-633F. The photodetector arrangement 630 may comprise a photodetector array, such as commercially available or custom imaging array circuits, or the like. Each of the photo detectors 635, and 630A-630F may be provided by portions of the overall photodetector array, and may thus be physically merged and/or indistinguishable in various embodiments. The various detectors may be distinguished simply by the pixel addressed that are associated with determining each of the various spot dimensions and positions that provide the measuring signals in a dual range focus detection arrangement that uses the elements 620 and 630, according to previously outlined principles.

The operation of the elements 620 and 630 shown in FIG. 6 may be generally understood by analogy with embodiments outlined in previous figures. Briefly, regarding the high resolution focus detection configuration, the high resolution focus sub-apertures 620A-620F may focus respective portions of an input wavefront to detector spots DSA-DSF respectively, on the high resolution photodetectors 633A-633F, provided by portions of the photodetector arrangement 630. In FIG. 6, the positions (pixel coordinates) of the "open" focus spots on the photodetectors 633A-633F indicate a flat input wavefront WF(ZNOM) and the corresponding workpiece surface distance Z=ZNOM, and the positions (pixel coordinates) of the filled focus spots DSA-DSF indicate a curved wavefront input (e.g., WF(+$\Delta$Z)) and the corresponding surface distance Z=ZNOM+$\Delta$Z. Various considerations with respect to finding the positions (pixel coordinates) for the detector spots DSA-DSF (e.g., by determined their centroid positions) are known in the art and are discussed in detail in the previously referenced '878 patent.

Briefly, regarding the broad range focus detection configuration, the broad range sub-aperture 625 may be located along the optical axis to transmit the central portion of an input wavefront to a detector spot DSBR on the broad range photodetector 635, provided by a portion of the photodetector arrangement 630. As previously outlined, the detector spot DSBR may have a dimension (e.g., a diameter, or area) that corresponds to the curvature of the input wavefront. In FIG. 6, the overall size of the "open" spot DSBR on the photodetector 635 indicates a flat input wavefront WF(ZNOM) and the corresponding workpiece surface distance Z=ZNOM, and the overall size of the concentric "filled" spot DSBR indicates a curved wavefront input (e.g., WF(+$\Delta$Z)) and the corresponding surface distance Z=ZNOM+$\Delta$Z. Various methods for finding spot dimensions on array detectors are known in the art and need not be described here (e.g., by establishing a diameter, or area, based on pixels having signals that exceed a threshold value, or the like). One method for finding a spot dimension on a photodetector configuration usable in place of the detector 635 is described in U.S. Pat. No. 5,113,386, to Whitehead et al., which is hereby incorporated by reference in its entirety.

It should be appreciated that the dual range focus detection arrangements outlined herein include a previously unknown and particularly advantageous combination of features. For example, the region of the wavefront proximate to the optical axis is advantageously used for a broad range focus detector configuration that is of a different type than a Shack-Hartmann configuration, even the though Shack-Hartmann configuration is used for the high resolution portion. This is advantageous because a Shack-Hartmann sub-aperture along the optical axis would be insensitive to wavefront curvature, and various broad range focus detector configurations have a simpler configuration or more reliable operation by having their input sub-aperture along the optical axis. Conversely, Shack-Hartmann sub-apertures located away from the optical axis are sensitive to wavefront curvature, as desired. In the disclosed combination of these features, the sub-apertures of the broad range and high resolution focus detection configurations may all sample the same wavefront without requiring beamsplitting surfaces or the like, in a dual range focus detector arrangement. In addition, a single detector array may provide all measurement signals associated with each of the sub-apertures, in some embodiments. It should be appreciated that although the broad range focus detector configurations illustrated herein have generally been "spot size" type detectors, other know types of suitable broad range focus detectors may be positioned with their sub-aperture located on, or proximate to, the optical axis (e.g., knife edge focus sensors, or the like), and may be used in place of the specific configuration disclosed herein. In various embodiments, the broad range focus detector configuration may put output a single broad range focus detector signal, or a signal that is derived from a plurality of photodetector signals (e.g., a difference signal), or it may directly output a plurality of photodetector signals (e.g., pixel outputs) that depend on the location of a workpiece surface, which may be processed externally to indicate the workpiece surface location.

Figure 7:
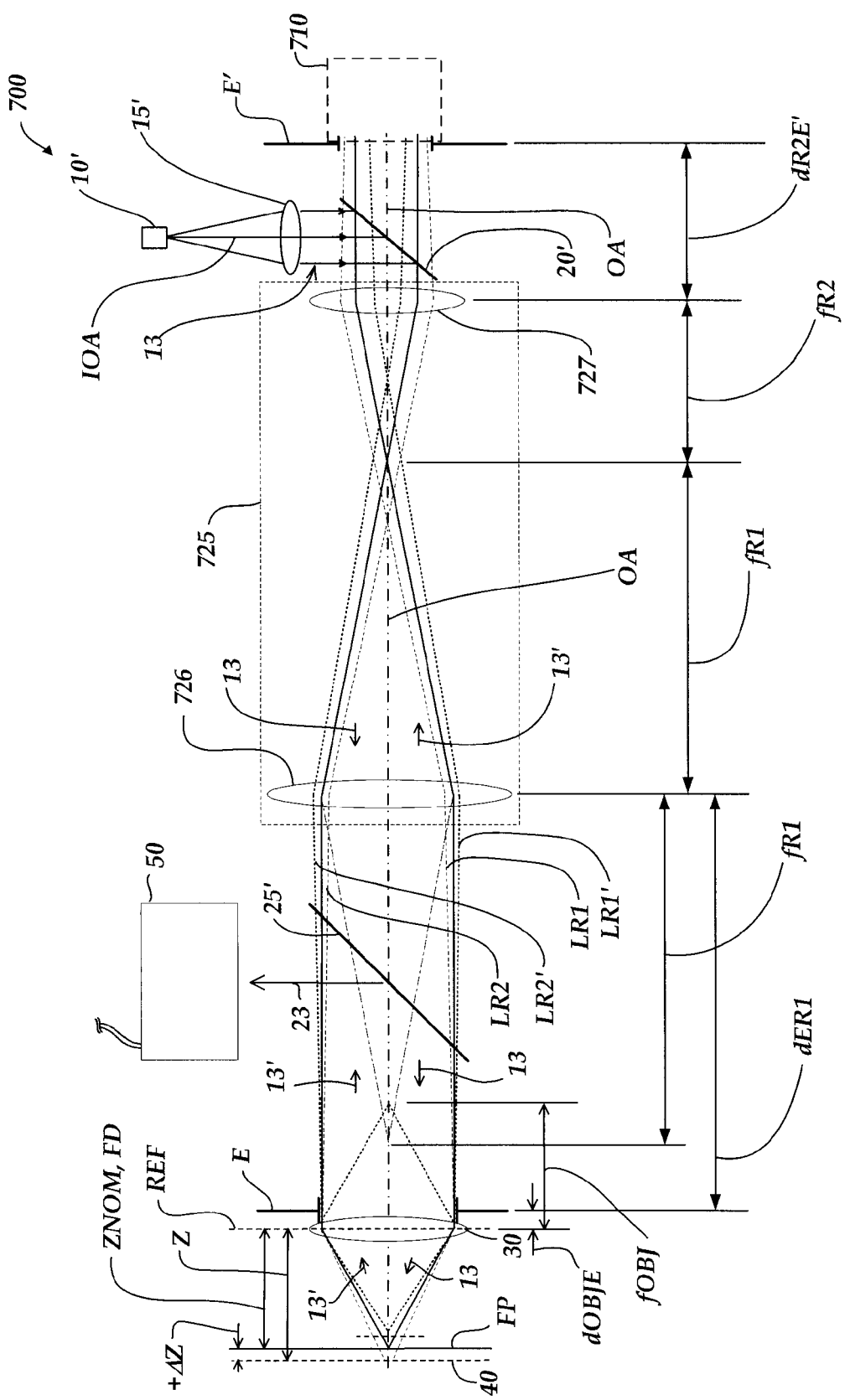
FIG. 7 is a diagram of a third embodiment of a focus sensor, which uses a second embodiment of a relay lens arrangement in combination with various focus detection arrangements.

FIG. 7 is a diagram of a third embodiment of a focus sensor 700 which uses a relay lens arrangement 725' in combination with either a dual range focus detection arrangement or single range focus detection arrangement. The components and operation of the focus sensor 700 are in many respects analogous to those of the focus sensor 500 of FIG. 5 and, in various embodiments; the components in FIG. 7 may be similar in form and/or function to similarly numbered components in FIG. 5 (e.g., the component 725 may be similar in function to the component 525), except as otherwise described below. Therefore, only the significant differences are emphasized in the following description. It should be appreciated that although the layout of the focus sensor 700 shown in FIG. 7 is a "linear" layout with a straight optical axis OA, this only done to more clearly present the relationship between various features and/or dimensions described further below. The optical axis OA could be configured similarly to previously described focus sensors using addition components, if desired.

The novel combination and arrangement of components in the focus sensor 700 provide a unique combination of benefits for a machine vision system focus sensor. FIG. 7 shows that the focus sensor 700 may include an objective lens 30 which has an objective lens pupil E, a beam splitting surface 25, a camera 50, a relay lens arrangement 725 comprising a first relay lens 726 and a second relay lens 727, a beam splitting surface 20', a collimation lens 15', an illumination source 10', and a focus detector arrangement 710 that has an entrance pupil E'. One particular difference between the focus sensor 700 and the focus sensor 500 shown in FIG. 5 is that the illumination source 10' and the beam splitting surface 20' are located to operate in an optical path between the second relay lens 727 and the focus detector arrangement 710. In comparison to the focus sensor 500, the resulting configuration provides a novel combination of benefits and is particularly advantageous in practical implementations, as described below Regarding operation of the focus sensor 700, radiation from the illumination source 10' is input to collimation lens 15' which outputs an illumination beam 13, as previously described, along an illumination optical axis IOA. The illumination beam 13 is reflected from the first beamsplitting surface 20', which deflects it to pass along the optical axis OA through the second relay lens 727 and the first relay lens 726 of the relay lens arrangement 725, and then through the second beamsplitting surface 25 and the objective lens 30. The objective lens 30 focuses the illumination beam 13 at a nominal focus plane FP, as previously described. A workpiece surface 40 reflects the focused illumination beam 13, as well as image light, in a reflected beam 13'. The illumination beam light included in the reflected beam 13' has a wavefront curvature which indicates the relationship between the workpiece surface 40 and the nominal focus plane FP, as previously described. The reflected beam 13' follows the previously described path, in reverse, except, at the second beam splitting surface 25, the image light which may be included in the reflected beam 13' is reflected to provide image light 23 to the camera 50, and the operative portion of the reflected beam 13' is transmitted at the first beam splitting surface 20' to pass through the entrance pupil E' and into the focus detector arrangement 710.

As described previously with reference to FIG. 5, in various embodiments it is desirable for the relay lens arrangement 725 to image the objective lens pupil E, in some embodiments. One advantage of the configuration of the focus sensor 700, in comparison to the focus sensor 500, is that the first relay lens 726 may be positioned closer to the second beam splitting surface 25' and the objective lens pupil E. Thus, the first relay lens 26 may satisfy this condition with a relatively shorter focal length in some embodiments. Thus, the focus sensor 700 may be both more economical and more compact than the focus sensor 500, allowing more practical implementations.

In the embodiment shown in FIG. 7, the relay lens arrangement 725 of the focus sensor 700 is configured to magnify the diameter of the illumination beam 13 as it passes through, such that it overfills, or approximately fills, the objective lens pupil E of the objective lens 30. It should be appreciated that in comparison to the illumination configuration shown in FIG. 5, this magnifying configuration allows a smaller collimation lens 15', a smaller beam splitting surface 20', and a shorter optical path length between the collimation lens 15' and the illumination source 10' (for a given source light divergence angle). All of these features of the focus sensor 700 allow it to be more economical and compact than the focus sensor 500, which is very important in practical implementations.

Another important advantage of the embodiment shown in FIG. 7, is that the relay lens arrangement 725 of the focus sensor 700 is configured to reduce the diameter of the reflected beam 13', which carries the curved wavefront that is sensed by the focus detector arrangement 710. As a result of the demagnification, the curvature of the wavefront is increased, which increases the sensitivity of the focus sensor 700.

Various advantageous design relationships will now be explained. In FIG. 7: dOBJE is the dimension from the location of the objective lens 30 to the objective lens pupil E, fOBJ is the objective lens focal length, dER1 is the dimension from the objective lens pupil E to the lens 726 (or more generally from the objective lens pupil E to the front principal plane of the relay lens arrangement 725), fR1 is the focal length of the first relay lens 726, fR2 is the focal length of the second relay lens 727, dR2 E' is the dimension from the second relay lens 727 to the entrance pupil E' of the focus detector arrangement 710 (or more generally from the entrance pupil E' to the back principal plane of the relay lens arrangement 725). As shown in FIG. 7, in various embodiments, the first relay lens 726 and the second relay lens 727 may be spaced apart by the sum of these focal lengths, to provide a magnification factor of (fR1/fR2). In one exemplary embodiment, the magnification factor may be approximately 2 (e.g., in the range 1.5 to 3), in order to provide the benefits outlined above, balanced against other practical design considerations.

In some embodiments, as previously indicated, it may be most advantageous for the first relay lens 726 to be spaced apart from the objective lens pupil E, by its focal length fR1, that is, dER1=fR1, in order to image the objective lens pupil E to a plane at, or in the vicinity of, the focus detector arrangement entrance pupil E'. However, in various embodiments the condition dER1=fR1 is not necessary, and the objective lens pupil E may be imaged to a plane at, or in vicinity of, the focus detector entrance pupil E', by satisfying other conditions, as described further below in relation to EQUATION 1.

In other embodiments, planes other than the plane of the objective lens pupil E may be imaged by the relay lens arrangement to a plane only roughly in the vicinity of the entrance pupil E' (e.g., an image plane located at an operable location in a range of +/−0.5*dR2E' from the entrance pupil), and acceptable operation may still result for suitably restricted lens configurations and practical focus ranges. In some cases, the objective lens pupil E may be located approximately at the objective lens principal plane, or between the objective lens principal plane and the relay lens arrangement. In such cases, the relay lens arrangement may be described more generally as imaging a plane between the objective lens and the relay lens arrangement, subject to practical constraints or conditions described in greater detail below. In the particular embodiment shown in FIG. 7, the focal length fR1 is less than the dimension dER1, that is, fR1<dER1. Such embodiments may be useful to overcome space or component placement constraints, or practical lens constraints, in some practical implementations. Such embodiments are permissible provided that the previously described "crossover" and other analogous "signal polarity reversing" effects are prevented at all locations along the optical axis OA for a specified focus sensing range. A general guideline for preventing crossover is that the focus detector is configured such that that rays of the reflected beam do not cross over one another prior to reaching the plane that is imaged by the relay lens arrangement, at least for those rays which are eventually input to the focus detector arrangement. One quantitative guideline for preventing crossover is ((fOBJ−dOBJE)+fR1)>dER1. However, independently, a specified focus sensing range that is appropriately limited may, in practice, also help prevent crossover. For example, as illustrated in FIG. 7, the rays LR1' and LR2' will not cause crossover because they are diverging, and for suitably restricted lens configurations converging rays represented by the rays LR1 and LR2 will not converge enough to cause crossover within practical focus sensing ranges. Furthermore, the operation of the focus sensor 700 is not very sensitive to the location of the image plane of the second relay lens 727. Thus, the second relay lens 727 need not image at the entrance pupil E', although this may be advantageous in various embodiments.

Regarding suitably restricted lens configurations, one description may be in terms of the objective lens focal length fOBJ since, qualitatively speaking, this may very roughly reflect how far from the objective lens (or objective lens pupil E) crossover will occur for a given amount of defocus +/−ΔZ. In particular, based on experience, in some practical embodiments acceptable operation has been provided when (dER1−fR1)<3.0*fOBJ. Other advantageous embodiments may be configured to satisfy the condition (dER1−fR1)<2.0*fOBJ, and other even more advantageous embodiments may be configured to satisfy the condition (dER1−fR1)<1.0*fOBJ. When interchangeable objective lenses are to be used in a focus sensor such as the focus sensor 700, fOBJ in the foregoing relationships should be the shortest focal length among the interchangeable lenses. Of course, if dER1 is approximately equal to fR1, a wide variety of interchangeable objective lenses may be used without concern.

As previously outlined, in various embodiments, the focal lengths of the first relay lens 726 and the second relay lens 727 need not match the dimensions dER1 and dR2E', respectively, in order to image the objective lens pupil E onto the focus detector arrangement entrance pupil E'. Rather, there are other conditions where the objective lens pupil E will be imaged onto the focus detector entrance pupil E'. For example, in an embodiment where a relay lens arrangement 725 provides a 2:1 magnification factor, the objective lens pupil E will be imaged onto the focus detector entrance pupil E' in any configuration that meets the following condition:

$$dR2E' = \frac{3}{4} * \left[ fR1 - \frac{dER1}{3} \right] \qquad \text{EQ. 1}$$

Analogous conditions exist for other magnification factors, as may be determined by one of ordinary skill in the art. Thus, in most implementations, the ideal of imaging the objective lens pupil E onto the focus detector arrangement entrance pupil E' may be fulfilled with suitable care in design.

As outlined above, as a result of demagnification of the reflected beam 13' by the relay lens arrangement 725, the curvature of the focus indicating wavefront in the reflected beam 13' is increased, which may increase the sensitivity of the focus sensor 700. Accordingly, if a dual range focus detector arrangement disclosed herein is used for the focus detector arrangement 710, then the additional sensitivity may be used to increase the resolution of the high resolution Shack-Hartman portion of the focus detector arrangement. Conversely, it is also possible to maintain the resolution of the high resolution Shack-Hartman portion, and use the additional sensitivity to extend its effective range (e.g., by using an objective lens with a lower numerical aperture). The focus sensor in FIGS. 8 and 9 takes the latter approach. As a result, in some embodiments, a dual range focus detector arrangement is not needed. Instead, a single range Shack-Hartmann focus detector arrangement may be used to provide a specified focus range that is satisfactory for a number of applications.

Figure 8:
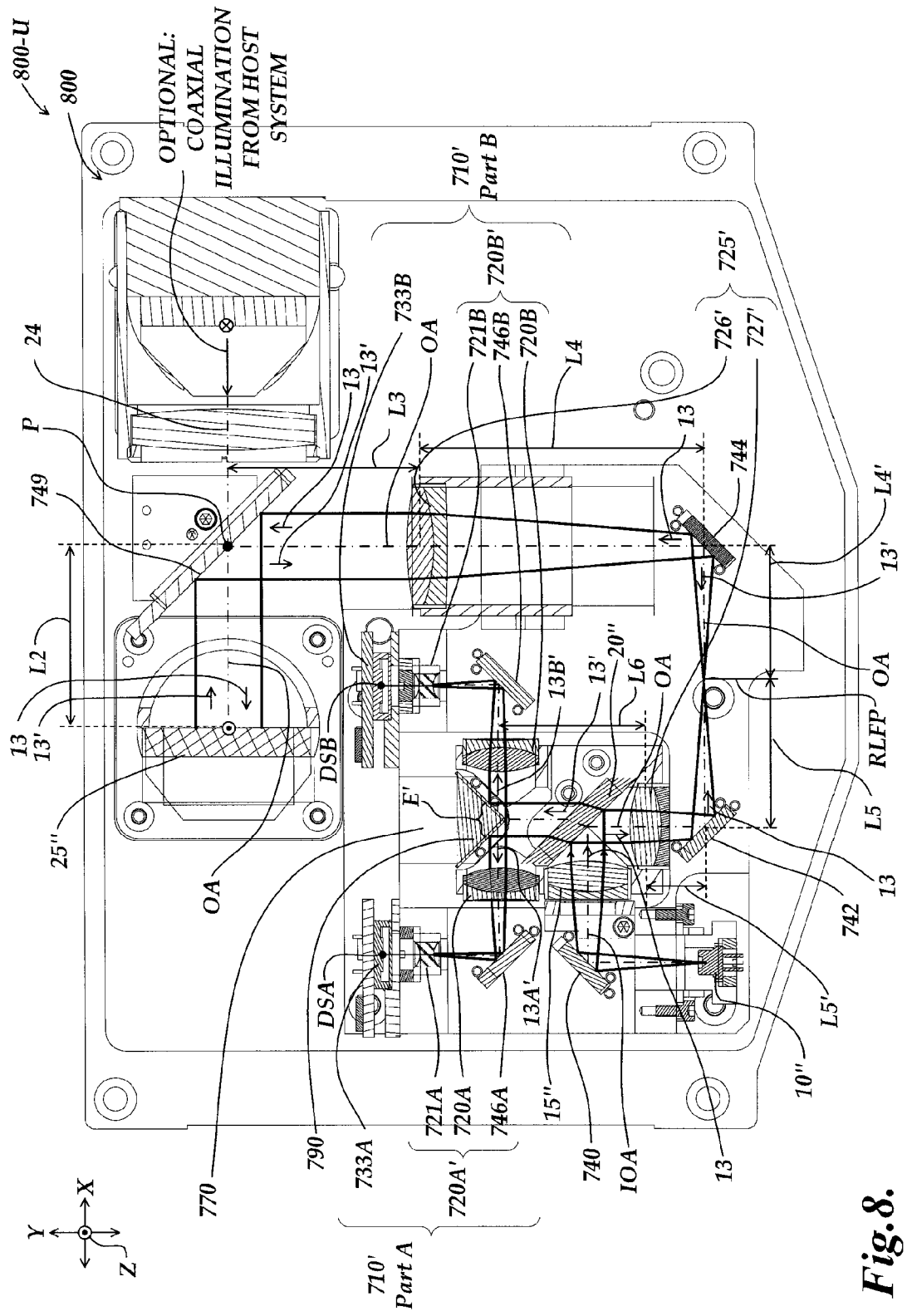
FIG. 8 is a diagram of a fourth embodiment of a focus sensor which uses a relay lens arrangement in combination with a single range Shack-Hartmann focus detection arrangement.
Figure 9:
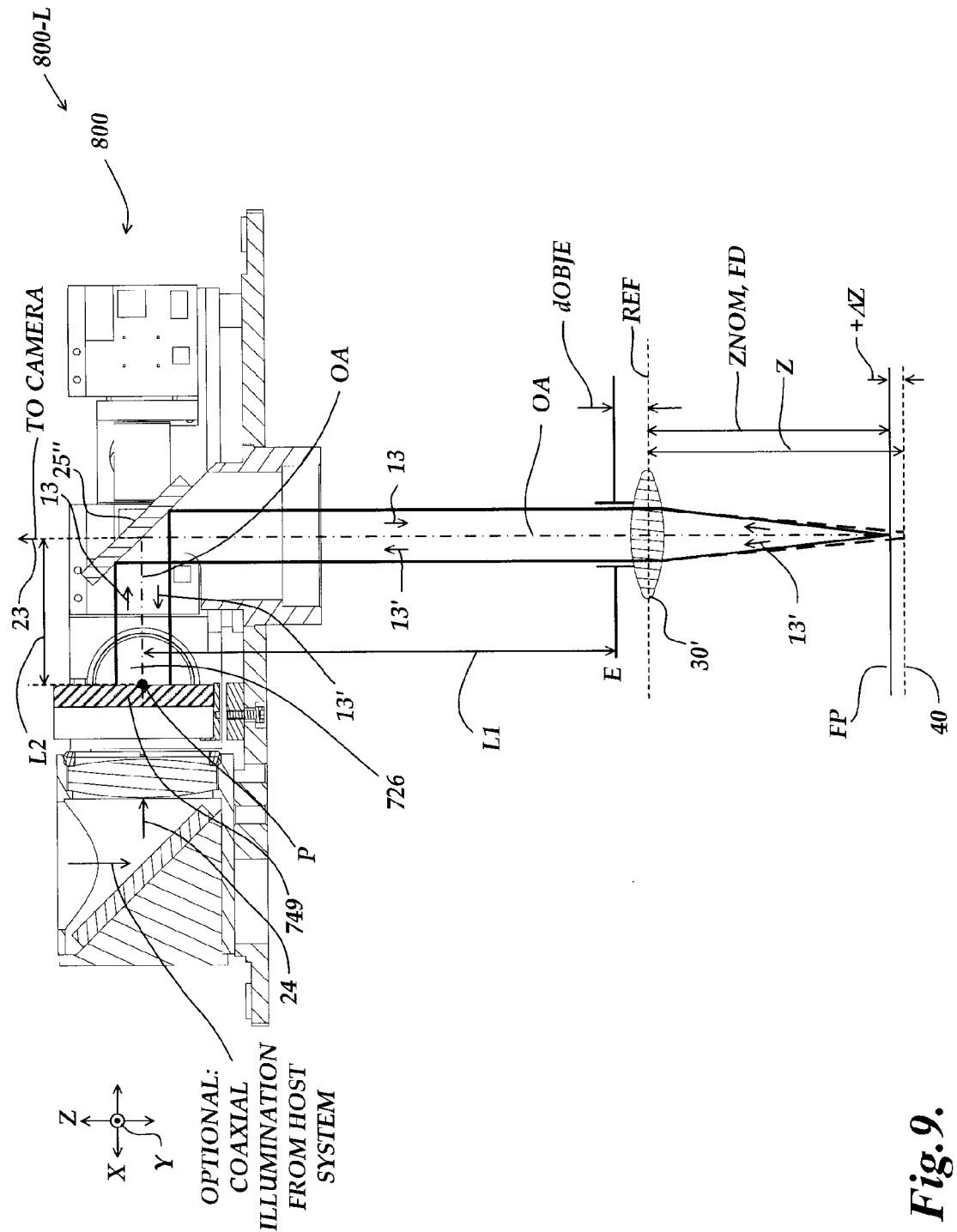
FIG. 9 is a diagram showing additional components of the focus sensor of FIG. 8.

FIGS. 8 and 9 are diagrams 800-U and 880-L showing upper and lower portions, respectively, of a fourth embodiment of an extended range focus sensor 800. The focus sensor 800 uses a relay lens arrangement 725' in combination with a single range Shack-Hartmann focus detector arrangement 710'. The components and operation of the focus sensor 800 are in many respects analogous to those of the focus sensor 700 of FIG. 7 and, in various embodiments; the components in FIGS. 8 and 9 may be analogous to similarly numbered components in FIG. 7 (e.g., the component 726' may be similar in function to the component 726), except as otherwise described below. Therefore, only the significant differences are emphasized in the following description. The primary differences between the focus sensor 800 and the focus sensor 700 of FIG. 7 include the addition of several turning mirrors 740-749 which are used in order to fold the optical axes OA and IOA into a compact configuration, and the use of a novel Shack-Hartmann focus detector arrangement 710'. The novel combination and arrangement of components in the focus sensor 800 provide a unique combination of benefits, and is particularly well adapted for integration into the optical systems of a machine vision inspection system.

As shown in FIG. 8, the primary components of the focus sensor 800 include an illumination source 10", a collimation lens 15", a first beam splitting surface 20", a focus detection arrangement 710' having an entrance pupil E'—as will be described in greater detail below, a relay lens arrangement 725' comprising first and second relay lenses 726' and 727', respectively, and a second beam splitting surface 25", which turns the operable beams of the focus sensor between the X-Y plane and the Z direction. Continuing in the Z direction along the optical axis OA, as shown in FIG. 9, the focus sensor 800 further includes an interchangeable objective lens 30' having an objective lens pupil E. The general operation and relationships between the components outlined above may be understood by analogy with the previous description of FIG. 7, and as described further below.

Regarding operation of the focus sensor 800, radiation from the illumination source 10" is directed to the turning mirror 740 and is then input to collimation lens 15" which outputs an illumination beam 13, along an illumination optical axis IOA. The illumination beam 13 is reflected from the first beam splitting surface 20". In the embodiment shown in FIG. 8, the first beam splitting surface 20" is provided by a beam splitting plate, rather than a cube, to avoid spurious reflections from a cube surface back along the optical axes IOA and/or OA. From the first beam splitting surface 20", the illumination beam 13 is deflected to pass along the optical axis OA through the second relay lens 727' which focuses it toward a turning mirror 742 and then on to a relay lens focal plane RLFP. As seen in FIG. 8, the focal length fR2 of the second relay lens equals the sum of distances (L5+L5'). From the relay lens focal plane RLFP the illumination beam 13 continues to the turning mirror 744 and is deflected to pass along the optical axis OA through the first relay lens 726', where the illumination beam 13 becomes collimated and passes on along the optical axis toward a turning mirror 749. As seen in FIG. 8, the focal length fR1 of the first relay lens equals the sum of distances (L4+L4'). The particular embodiment of the relay lens arrangement 725' shown in FIG. 8 provides a magnification factor of 2:1. Thus, similar to features described with reference to FIG. 7, the illumination arrangement of the focus sensor 800 is compact and produces a relatively small diameter illumination, which is magnified to the desired diameter (e.g., for filling the objective lens pupil of the objective lens) by passing through the relay lens arrangement 725'. Continuing from the turning mirror 749 the collimated illumination beam 13 is reflected toward the second beam splitting surface 25" which, as best seen in FIG. 9, turns the collimated illumination beam 13 from the X-Y plane to be aligned along the Z direction, in this embodiment. The illumination beam then passes along the optical axis OA to pass through the objective lens pupil E and the objective lens 30'. As shown in FIGS. 8 and 9, the dimension from the objective lens pupil E to the first relay lens 726', designated dER1, equals the sum of distances (L1+L2+L3).

The objective lens 30 focuses the illumination beam 13 at a nominal focus plane FP, as previously described. A workpiece surface 40 reflects the focused illumination beam 13, as well as image light, in a reflected beam 13'. The illumination beam light included in the reflected beam 13' has a wavefront curvature which indicates the relationship between the workpiece surface 40 and the nominal focus plane FP, as previously described. The reflected beam 13' follows the previously described path, in reverse, except at the second beam splitting surface 25" the image light, which may be included with the reflected beam 13' in some embodiments, is transmitted to provide image light 23, which may be directed to a camera of a host machine vision inspection system, in some embodiments. In some embodiments, various beam splitting surfaces and turning mirrors may include a suitable dichroic coating, in order to efficiently convey the focus sensor beams, while also allowing efficient use of white light for imaging. From the second beam splitting surface 25" the reflected beam 13' continues in reverse along the previously described path of the illumination beam 13, except the operative portion of the reflected beam 13' is transmitted at the first beam splitting surface 20" to the entrance pupil E' of the focus detector arrangement 710'. It will be appreciated the due to the 1:2 reduction factor provided for the reflected beam 13' by the relay lens arrangement 725', the included wavefront curvature is increased, which increases the signal of the Shack-Hartmann focus detector arrangement, and thus the sensitivity of the focus sensor 800, as previously described. A further benefit of the reduced diameter of the reflected beam 13' is that it allows smaller, more economical, optical components and layout for the Shack-Hartmann focus detector arrangement 710'.

The embodiment of the Shack-Hartmann focus detector arrangement 710' shown in FIG. 8, is uniquely configured to be used in combination with various features outlined above, to further increase the sensitivity of the focus sensor 800 relative previously disclosed configurations. In the embodiment shown in FIG. 8, the significant components of the Shack-Hartmann focus detector arrangement 710' include symmetric portions 710' part A, and 710' part B, and a central 90° beam splitting prism or mirror 790.

The benefit of the increased curvature of the reduced reflected beam 13' cannot be practically realized with the previously disclosed Shack-Hartmann configurations that use side-by-side sub-aperture lenses. Accurate lenses small enough to be positioned side-by-side in the reduced reflected beam 13' are not readily available, and even if they were, a great portion of the light of the reflected beam 13' would fall outside of such sub-aperture lenses, lowering the signal to noise ratio of the detector. In contrast, the focus detector arrangement 710' takes advantage of the small beam diameter. In effect, the entrance pupil E' of the detector arrangement 710 is provided by the intersection of the reflected beam 13' and the beam splitting prism 790, such that the detector arrangement 710' uses all available light.

Each of the symmetric portions 710' part A and 710' part B includes components respectively designated with an A or B suffix, including a lens 720, a turning mirror 746, a deflection enhancing lens 721, and a photodetector 733. In operation, the beam splitting prism 790 divides the reflected beam 13', regardless of its size, and turns the two halves of the beam in opposite directions, which allows a layout that uses accurate, economical, and readily available components. In each symmetric portion 710' part A or 710' part B, the half-beam carrying the wavefront curvature is directed through the lens 720, and which focuses the half-beam and provides and initial lateral deflection that depends on its wavefront curvature. In this embodiment, the lens 720 is not a limiting aperture. Rather, it transmits all the light of the half-beam. The resulting half beam continues to the turning mirror 746 and is directed toward the deflection enhancing lens 721. The deflection enhancing lens 721, which in this embodiment is a negative lens arranged in a novel configuration that is relatively farther along the optical path from the lens 720 and relatively closer to the photodetector 733 (e.g., at least two times farther from the lens 720 than from the photodetector 733), provides an additional lateral beam deflection that depends on where it receives the nearly focused, initially deflected half beam. In another embodiment, a positive lens, such as a ball lens, may be used for the deflection enhancing lens. After being transmitted through the deflection enhancing lens 721, the additionally deflected half beam is focused at a spot DS on the detector 733. The photodetector 733 may comprise any of the photodetectors previously described herein. In one embodiment, the photodetector 733 is a lateral effect photodiode.

The spots DSA and DSB from the two parts of the focus detector arrangement 710' provide corresponding signals which may be processed as previously described herein to provide an indication of $\Delta Z$ and/or the associated defocus (e.g., similarly to the signals corresponding the spots DSA and DSB and their related processing, as described with reference to FIGS. 2A-2C.) In another embodiment, the beam splitting prism 790 may be replaced by a conventional beamsplitting surface (e.g., 50% transmissive and 50% reflective surface), which provides two sub-beams from the reflected beam 13', one of which is transmitted straight through the beamsplitting surface. Components similar or identical to those outlined above, e.g., those of part 710' Part A, may be "repositioned" to receive and guide the transmitted beam to provide a functionally analogous focused spot DSA on a detector 733A. More generally, any single range Shack-Hartmann focus detector arrangement that provides a desired size, accuracy and range may be used.

The embodiment of the focus sensor 800 shown in FIGS. 8 and 9 is one example of a configuration wherein the objective lens pupil E is not necessarily imaged onto the focus detector entrance pupil E'. For example, in one embodiment, the optical path length from the second relays lens to the lenses 720A and 720B is approximately the same as the focal length fR2 of the second relay lens 727', and the optical path length to the entrance aperture E' is approximately 10 mm less. The focal length fOBJ of the objective lens 30' is approximately 40 mm, the focal length fR1 of the first relay lens 726' is 60 mm and the dimension dER1 from the exit aperture E to the first relay lens 726' is approximately dER1=(L1+L2+L3)=(55 mm+26.5 mm+26 mm)=107.5 mm. Thus, in this embodiment, (dER1−fR1)<1.2*fOBJ, which is a suitably restricted lens configuration according to previously disclosed limiting conditions. This embodiment also comes relatively close to satisfying the condition of EQUATION 1. In practice, the foregoing embodiment is suitable for a number of practical applications, and provides a usable focus range which may be on the order of 8 millimeters for a 2.5× objective lens having a depth of field of approximately 17 microns, or more generally a usable focus range on the order of 450 "depths of field" for any objective lens that is compatible with the design conditions outlined herein. Despite this rather large focus detection range, in other embodiments it may be more advantageous to configure dR2E' and/or fR1 and/or dER1 such that they fulfill the condition given by EQUATION 1, which images the objective lens pupil E onto the focus detector entrance pupil E'.

While the preferred embodiment of the invention has been illustrated and described, numerous variations in the illustrated and described arrangements of features and sequences of operations will be apparent to one skilled in the art based on this disclosure. Thus, it will be appreciated that various changes can be made therein without departing from the spirit and scope of the invention.

The embodiments of the invention in which an exclusive property or privilege is claimed are defined as follows:

1. A focus sensor for providing focus detection signals that depend on the location of a workpiece surface within a focus detection range along a direction approximately parallel to the optical axis of an objective lens, the focus sensor comprising:
    an illumination source;
    a collimation lens configured to input radiation from the illumination source and output an illumination beam having a fixed degree of collimation;
    an objective lens configured to input the illumination beam and to focus the illumination beam at a nominal focal plane along an optical axis of the focus sensor and to receive and transmit a reflected beam reflected from a workpiece surface located along the optical axis;
    a focus detector arrangement positioned along the optical axis to receive light from the reflected beam that is transmitted by the objective lens; and
    a first beamsplitting surface positioned along the illumination beam between the objective lens and the collimation lens, and along the reflected beam between the objective lens and the dual range focus detector arrangement,
    wherein the focus detector arrangement is a dual range focus detector arrangement comprising:
        a broad range focus detector configuration that is configured according to a first focus detection principle, and configured to provide at least one broad range focus detector signal that varies monotonically over a first focus detection range of the focus sensor, the broad range focus detector configuration including a broad range sub-aperture located proximate to the optical axis, and a broad range photodetector arranged to receive transmitted light from the broad range sub-aperture and output the at least one broad range focus detector signal; and
        a high resolution focus detector configuration that is configured according to a second focus detection principle that is different than the first focus detection principle, and configured to provide at least one high resolution focus detection signal over a second focus detection range that is smaller than, and located within, the first focus detection range, the high resolution focus detector configuration including at least one respective high resolution sub-aperture located proximate to the broad range sub-aperture and located off the optical axis, and a respective high resolution photodetector arranged to receive transmitted light from the respective high resolution sub-aperture and output a high resolution focus detector signal.

2. The focus sensor of claim 1, wherein the optical axis passes through the broad range sub-aperture element and the broad range sub-aperture element comprises a focus-altering lens that focuses the light that is transmitted to the broad range photodetector at a focus point beyond a detection plane of the broad range photodetector along the optical axis direction, for all reflected beams corresponding to the first focus detection range.

3. The focus sensor of claim 1, wherein the high resolution focus detector configuration is configured according to a Shack-Hartmann focus detection principle, the high resolution focus detector configuration including at least first and second respective high resolution sub-apertures located proximate to the broad range sub-aperture and located off the optical axis, and at least first and second respective high resolution photodetectors arranged to receive transmitted light from the respective high resolution sub-apertures, wherein the at least first and second respective high resolution photodetectors output at least first and second respective high resolution focus detector signals over the second focus detection range.

4. The focus sensor of claim 3, wherein the first and second respective high resolution focus detector signals depend on the location of the workpiece surface relative to the nominal focal plane, and a high resolution difference signal between the first and second respective high resolution focus detector signals is indicative of the location of the workpiece surface.

5. The focus sensor of claim 1, further comprising a relay lens arrangement located along the optical axis between the objective lens and the dual range focus detector arrangement, wherein the relay lens arrangement is configured to input the reflected beam that is transmitted by the objective lens and to image an objective lens pupil located proximate to the objective lens along the optical axis to an image plane at a location of dual range focus detector entrance pupil proximate to the sub-apertures of the dual range focus detector arrangement along the optical axis.

6. The focus sensor of claim 1, wherein:
    the broad range focus detector configuration is configured according to a first focus detection principle that is not a Shack-Hartmann focus detection principle, and is configured such that the optical axis passes through the broad range sub-aperture element; and
    the high resolution focus detector configuration is configured according to a Shack-Hartmann focus detection principle, and is configured to provide at least first and second high resolution focus detection signals over a second focus detection range that is smaller than, and located within, the first focus detection range, the high resolution focus detector configuration including at least first and second respective high resolution sub-apertures located proximate to the broad range sub-aperture and located off the optical axis, and first and second respective high resolution photodetectors arranged to receive transmitted light from the at least first and second respective high resolution sub-apertures and to output at least first and second high resolution focus detector signals.

7. The focus sensor of claim 6, further comprising a relay lens arrangement located along the optical axis between the objective lens and the dual range focus detection arrangement, wherein the relay lens arrangement is configured to input the reflected beam that is transmitted by the objective lens and to image an objective lens pupil located proximate to the objective lens along the optical axis to an image plane at a location of a dual range focus detector entrance pupil that is proximate to the sub-apertures of the dual range focus detector arrangement along the optical axis.

8. The focus sensor of claim 1, wherein the focus sensor is integrated into a precision machine vision inspection system and the objective lens comprises an objective lens of the precision machine vision inspection system.

9. A focus sensor for providing focus detection signals that depend on the location of a workpiece surface within a focus detection range along a direction approximately parallel to the optical axis of an objective lens, the focus sensor comprising:

an illumination source;
a collimation lens configured to input radiation from the illumination source and output an illumination beam having a fixed degree of collimation;
the objective lens configured to input the illumination beam and to focus the illumination beam at a nominal focal plane along an optical axis of the focus sensor and to receive and transmit a reflected beam reflected from a workpiece surface located along the optical axis;
a focus detector arrangement positioned along the optical axis to receive light from the reflected beam that is transmitted by the objective lens;
a first beamsplitting surface positioned along the illumination beam between the objective lens and the collimation lens, and along the reflected beam between the objective lens and the focus detector arrangement; and
a relay lens arrangement located along the optical axis between the objective lens and the focus detector arrangement, the relay lens arrangement configured to input the reflected beam that is transmitted by the objective lens and to output the reflected beam to be input by the focus detector arrangement,
wherein:
the focus detector arrangement comprises components configured according to a Shack-Hartmann focus detection principle; and
the focus sensor is configured such that at least one of the conditions (A) and (B) is fulfilled, wherein the condition (A) comprises:
(A) the relay lens arrangement is configured to image a first plane approximately coinciding with a location of an objective lens pupil of the objective lens along the optical axis to an image plane located in the vicinity of a focus detector entrance pupil of the focus detector arrangement; and
the condition (B) comprises:
(B) the focus detector arrangement is a single range Shack-Hartmann focus detector arrangement comprising:
a beamsplitting element arranged to receive the reflected beam input by the focus detector arrangement, such that the reflected beam is split into first and second split portions; and
first and second sets of components, each set of components comprising a first deflection lens, a deflection enhancing lens, and a photodetector, wherein the first deflection lens is arranged to receive a respective one of the split portions and to deflect that split portion depending on its wavefront curvature, and to focus that deflected split portion along an optical path and through the deflection enhancing lens to be focused approximately at the photodetector.

10. The focus sensor of claim 9, wherein the first beamsplitting surface is located along the optical axis between the relay lens arrangement and the focus detector arrangement, and is arranged such that it deflects the illumination beam output by the collimation lens to pass through the relay lens arrangement.

11. The focus sensor of claim 10, wherein the relay lens arrangement is configured to magnify the illumination beam by a magnification factor.

12. The focus sensor of claim 11, wherein the magnification factor is in a range from 1.5 to 3.0.

13. The focus sensor of claim 9, wherein a dimension between the front principal plane of the relay lens arrangement and the objective lens pupil is dER1, a dimension between the back principal plane of the relay lens arrangement and the focus detector entrance pupil is dR2E', a front focal length of the relay lens arrangement is fR1, a back focal length of the relay lens arrangement is fR2, a focal length of the objective lens is fOBJ, and the focus sensor is configured such that (dER1−fR1)<(K*fOBJ), where K is less than 3.0.

14. The focus sensor of claim 13, wherein K is less than 2.0.

15. The focus sensor of claim 14, wherein K is less than 1.0.

16. The focus sensor of claim 13, wherein the focus sensor is configured such that the image plane is located within a range of +/−0.5*dR2E' from the focus detector entrance pupil.

17. The focus sensor of claim 16, wherein the image plane approximately coincides with a location of the focus detector entrance pupil.

18. The focus sensor of claim 17, wherein fR1 is nominally equal to dER1.

19. The focus sensor of claim 9, wherein the focus sensor is configured to fulfill condition (B).

20. The focus sensor of claim 19, wherein the deflection enhancing lens as at least two times farther from the first deflection lens than it is from the photodetector.

21. The focus sensor of claim 19, wherein the beamsplitting element is a 90° beam splitting prism that reflects the first and second beam portions along opposite directions.

22. The focus sensor of claim 9, wherein the relay lens arrangement comprises a first relay lens arranged to input the reflected beam and to transmit it to a second relay lens that is arranged to output the reflected beam to be input by the focus detector arrangement.

23. The focus sensor of claim 9, wherein the focus sensor is integrated into a precision machine vision inspection system and the objective lens comprises an objective lens of the precision machine vision inspection system.

24. The focus sensor of claim 23, wherein the focus sensor further comprises a second beamsplitting surface located along the optical axis between the first relay lens arrangement and the objective lens, and furthermore located along an imaging path between the objective lens and a camera of the precision machine vision inspection system.

* * * * *